(12) United States Patent
Hirata et al.

(10) Patent No.: US 10,433,892 B2
(45) Date of Patent: Oct. 8, 2019

(54) THREE-DIMENSIONAL STRUCTURE PRODUCED FROM A MATERIAL CONTAINING POLYHYDROXYALKANOATE, KIT FOR PREPARATION OF BONE FILLER, AND INTRAMEDULLARY ROD

(71) Applicants: National University Corporation Nagoya University, Nagoya-shi, Aichi (JP); NATIONAL UNIVERSITY CORPORATION NAGOYA INSTITUTE OF TECHNOLOGY, Nagoya-shi, Aichi (JP)

(72) Inventors: Hitoshi Hirata, Aichi (JP); Takanobu Nishizuka, Aichi (JP); Tadahiro Natsume, Aichi (JP); Toshihiro Kasuga, Aichi (JP)

(73) Assignees: National University Corporation Nagoya University, Aichi (JP); National University Corporation Nagoya Institute of Technology, Aichi (JP)

( * ) Notice: Subject to any disclaimer, the term of this patent is extended or adjusted under 35 U.S.C. 154(b) by 419 days.

(21) Appl. No.: 14/388,627

(22) PCT Filed: Mar. 26, 2013

(86) PCT No.: PCT/JP2013/058809
§ 371 (c)(1),
(2) Date: Sep. 26, 2014

(87) PCT Pub. No.: WO2013/146788
PCT Pub. Date: Oct. 3, 2013

(65) Prior Publication Data
US 2015/0057669 A1    Feb. 26, 2015

(30) Foreign Application Priority Data
Mar. 27, 2012 (JP) ................. 2012-070746

(51) Int. Cl.
*A61B 17/58* (2006.01)
*A61B 17/88* (2006.01)
(Continued)

(52) U.S. Cl.
CPC ...... *A61B 17/8808* (2013.01); *A61L 24/0015* (2013.01); *A61L 24/06* (2013.01); *A61L 31/06* (2013.01); *A61L 2430/02* (2013.01)

(58) Field of Classification Search
CPC ...... A61L 31/06; A61L 2430/02; A61L 24/06; A61B 17/8808
(Continued)

(56) References Cited

U.S. PATENT DOCUMENTS 6,514,515 B1 * 2/2003 Williams ............ A61L 27/18
424/424
6,548,569 B1 * 4/2003 Williams ............ C08K 5/0033
521/27
(Continued)

FOREIGN PATENT DOCUMENTS

JP    2000-262609 A    9/2000
JP    2002-539854 A    11/2002
(Continued)

OTHER PUBLICATIONS

Saikku-Backstrom, et al., "Intramedullary fixation of cortical bone osteotomies with absorbable self-reinforced fibrillated poly-96L/4D-lactide (SR-PLA96) rods in rabbits," Biomaterials, vol. 22, No. 1 (2001) pp. 33-43.
(Continued)

*Primary Examiner* — Zade Coley
*Assistant Examiner* — Jessica Weiss
(74) *Attorney, Agent, or Firm* — McDermott Will & Emery LLP

(57) ABSTRACT

Provided is a material for preventing bone cement from leaking out from bone during packing of the bone cement
(Continued)

into a bone fracture site. The bone cement can be prevented from leaking out from the bone by employing a three-dimensional structure produced from a material containing a polyhydroxyalkanoate, when packing the bone cement into the bone fracture site.

14 Claims, 15 Drawing Sheets

(51) Int. Cl.
*A61L 31/06* (2006.01)
*A61L 24/00* (2006.01)
*A61L 24/06* (2006.01)

(58) Field of Classification Search
USPC ..... 606/92–95; 528/196, 198, 271–272, 274, 528/351, 352, 354; 525/361; 424/422, 424/424, 425, 484
See application file for complete search history.

(56) References Cited

U.S. PATENT DOCUMENTS

| | | | |
|---|---|---|---|
| 7,641,825 B2* | 1/2010 | Rizk | A61L 17/105 264/103 |
| 8,007,498 B2* | 8/2011 | Mische | A61B 17/7258 606/100 |
| 8,034,270 B2* | 10/2011 | Martin | A61F 2/0063 264/103 |
| 2002/0156150 A1 | 10/2002 | Williams et al. | |
| 2006/0246584 A1 | 11/2006 | Covelli | |
| 2008/0033077 A1* | 2/2008 | Hashimoto | C08L 51/04 524/9 |
| 2008/0061467 A1* | 3/2008 | Iwata | D01F 6/625 264/210.5 |
| 2008/0188945 A1* | 8/2008 | Boyce | A61B 17/0401 623/23.61 |
| 2008/0255560 A1 | 10/2008 | Myers et al. | |
| 2009/0299373 A1 | 12/2009 | Sisken | |
| 2010/0063598 A1 | 3/2010 | Hirata et al. | |
| 2010/0203155 A1* | 8/2010 | Wei | A61F 2/4603 424/549 |
| 2010/0204699 A1* | 8/2010 | Wei | A61F 2/4603 606/76 |
| 2010/0229258 A1* | 9/2010 | Bohmert-Tatarev | C12N 15/8214 800/278 |
| 2011/0245922 A1 | 10/2011 | Kasuga et al. | |
| 2012/0114756 A1* | 5/2012 | Emanuel | A61K 9/1617 424/486 |
| 2012/0150285 A1* | 6/2012 | Cahil | A61L 27/18 623/1.46 |
| 2014/0178346 A1* | 6/2014 | Byrne | A61K 35/12 424/93.21 |
| 2014/0287018 A1* | 9/2014 | Soo | A61C 8/0016 424/423 |
| 2016/0144067 A1* | 5/2016 | Armbruster | A61B 17/80 604/307 |

FOREIGN PATENT DOCUMENTS

| | | |
|---|---|---|
| JP | 2006-506108 A | 2/2006 |
| JP | 2008-500140 A | 1/2008 |
| JP | 2011-212039 A | 10/2011 |
| WO | 2005/112804 A1 | 12/2005 |
| WO | 2008/026596 A1 | 3/2008 |
| WO | 2008/057212 A1 | 5/2008 |
| WO | 2009/085823 A1 | 7/2009 |
| WO | 2010/075530 A1 | 7/2010 |

OTHER PUBLICATIONS

K. Zhao, et al., "Polyhydroxyalkanoate (PHA) scaffolds with good mechanical properties and biocompatibility," Biomaterials, vol. 24, No. 5, 2003, pp. 1041-1045.
International Search Report issued in International Application PCT/JP2013/058809 dated Jun. 18, 2013, with English translation.
Supplementary European Search Report EP Application No. 13 77 0377 dated Jul. 30, 2015.
Office Action issued in corresponding European Patent Application No. 13770377.3, dated Jul. 19, 2018.

* cited by examiner (a)

(b)

(c)

(a)

(b)

10,433,892 B2

THREE-DIMENSIONAL STRUCTURE PRODUCED FROM A MATERIAL CONTAINING POLYHYDROXYALKANOATE, KIT FOR PREPARATION OF BONE FILLER, AND INTRAMEDULLARY ROD

RELATED APPLICATIONS

This application is the U.S. National Phase under 35 U.S.C. § 371 of International Application No. PCT/JP2013/058809, filed on Mar. 26, 2013, which in turn claims the benefit of Japanese Application No. 2012-070746, filed on Mar. 27, 2012, the disclosures of which are incorporated by reference herein.

TECHNICAL FIELD

The present invention relates to a three-dimensional structure produced from a material containing a polyhydroxyalkanoate; a kit for preparation of a bone filler; and an intramedullary rod, which are suitable for treatment of bone that has become brittle due to osteoporosis.

TECHNICAL BACKGROUND

As society ages, cases of osteoporosis and bone fragility fractures have been on the increase in recent years. Each year, 150,000 cases of femoral neck bone fracture occur, necessitating 250,000,000,000 yen in medical costs. A considerable number of these are bone fragility fractures that are not caused by a fall. While bone fragility fractures do not initially involve dislocation (meaning that the bone fractured bone shifts or turns, as a result of which the dislocated region visibly appears to change shape), dislocation proceeds gradually, ultimately leading to highly invasive and expensive surgical procedures.

The typical surgical procedures employed for a bone fracture site are a locking plate procedure in which a metal plate is positioned against the bone fracture region, and the plate fastened to the bone with screws; and an intramedullary rod fastening procedure in which a long rod made of metal is implanted into the medullary cavity at the center of the bone from the end of the bone, and the rod fastened with screws. However, when the aforedescribed surgical procedures are performed on patients with osteoporosis or a bone fragility fracture, because the strength of the bone is less than the strength of the metal, various problems such as loosening and re-dislocation have occurred.

Another known surgical procedure for bone fracture sites is a method in which the bone marrow is scraped out, a structural framework furnished with a sheathing formed from a bioabsorbable material or the like is inserted therein, and once inserted the structural framework is expanded and packed with bone cement (see Patent Document 1).

More recently, balloon kyphoplasty, which is a technique used for patients whose pain caused by a spinal bone fracture due to osteoporosis does not improve, became covered by insurance starting in January of 2011, and has come to be commonly used in Japan. This method is noted for being a relatively non-invasive treatment method, and involves (1) insertion, from the patient's back, a small instrument with an attached balloon into a bone fracture region of the spine, (2) expanding the balloon within the vertebra to restore the broken bone to its shape prior to bone fracture, (3) then withdrawing the balloon to form a cavity inside the vertebra, and (4) packing bone cement into the cavity so formed to fill the cavity, by a surgery which can be completed in about one hour.

However, problems encountered with balloon kyphoplasty include (1) by first inserting a balloon made of silicone, and using the balloon to squeeze and crush the substantia spongiosa, which is the spongy bone inside the marrow, to create a wall and ensure a space, it is possible to reliably inject bone cement into the target region while preventing leakage, but since the hard bone (cortical bone) surrounding the bone fracture site is crushed, leaking from this area cannot be prevented; (2) the bone cement employed in balloon kyphoplasty is a not a calcium bone cement, instead employing a resin known as methyl methacrylate. While this resin has excellent strength and can reliably increase bone strength quickly, the material is unable to directly bond with bone, and during curing emits heat to around 90 degrees, thus affecting surrounding tissue; and (3) as the cured methyl methacrylate is too rigid, when used in patients who have brittle bones to begin with, bone fractures are sometimes induced in regions of bone that have weaker strength than the cured methyl methacrylate and that surround the site where it is used.

Furthermore, if the bone cement at a packing site should leak out from the bone and flow into blood vessels, there is a risk of causing a pulmonary embolism. To solve this problem, during packing of bone cement into a bone defect region such as a bone fracture site or the like, it is known to encapsulate the bone cement paste in a bioabsorbable material comprising one or more materials selected from fibrin sheets, collagen sheets, and homopolymers or copolymers of poly(lactic acid) and Poly(glycolic acid), in order to prevent the bone cement from leaking, and to prevent delayed curing time (see Patent Document 2).

Also known is a flocculant three-dimensional structure formed from a controlled release system of a chemical composition for effectively eliciting bone reconstruction capability, and, as a material for providing good fitting to the affected part, a siloxane-containing substance having as the principal component a synthetic polymer such as poly(lactic acid) (PLA), a copolymer of poly(lactic acid) and poly (glycolic acid) (PGA), polyethylene glycol (PEG), polycaprolactone (PCL), or a copolymer of PLA, PGA, PEG, and PCL, or a natural polymer such as fibrin, collagen, alginic acid, hyaluronic acid, chitin, chitosan, or the like (see Patent Document 3).

However, during packing of bone cement into a bone fracture site, it is necessary to induce the tacky bone cement paste to penetrate into every corner of the irregularly shaped medullary cavity, leaving no gaps. The sheath of the aforedescribed Patent Document 1 is manufactured from materials such as collagen, polyester fibers, poly(lactic acid), and the like, and lacks pliability, making close adhesion to bone a problem.

The bioabsorbable material indicated in the aforedescribed Patent Document 2, and the three-dimensional structure indicated in the aforedescribed Patent Document 3, lack excellent elongation, and therefore cannot withstand the pressure produced during injection of the bone cement paste, thus presenting the problem of a risk of the bone cement leaking out from the three-dimensional structure and, as a result, flowing into blood vessels, as well as difficulty in packing the viscous bone cement paste into every corner of the bone.

Additionally, the structural backbone indicated in the aforedescribed Patent Document 1, and most other such intramedullary rods designed to reinforce a bone fracture site from inside the bone, are produced from metal, and if a re-fracture occurs subsequent to the surgical procedure, the metal can break loose from the bone at the bone fracture site, with a risk of injury to biological tissue.

Meanwhile, in the case of packing only an osteoconductive calcium phosphate-based bone cement without the use of an intramedullary rod for surgery at a bone fracture site, the bone cement in the cured state lacks elasticity, posing a risk of breaking due to stress created by bending, pulling, compression, and the like. For example, when used in a (spinal) bone fracture of a patient who has suffered a compression bone fracture of the spine due to osteoporosis, the cured calcium phosphate-based bone cement does not adequately maintain mechanical strength for extended periods under conditions of being subjected to relatively high pressure, and it was difficult to consistently maintain the desired shape. Therefore, a filler material in which fibers having crimp are dispersed in a calcium phosphate-based bone cement is known (see Patent Document 4), but this material is not fully satisfactory in terms of bending and tensile strength.

PRIOR ARTS LIST

Patent Documents

Patent Document 1: Japanese Laid-open Patent Publication 2008-500140
Patent Document 2: Japanese Laid-open Patent Publication 2000-262609
Patent Document 3: Japanese Laid-open Patent Publication 2011-212039
Patent Document 4: International Patent Application 2008/026596

SUMMARY OF THE INVENTION

Problems to be Solved by the Invention

The present invention is intended to solve the aforedescribed problems of the prior art, and is the result of painstaking research leading to the discoveries that a three-dimensional structure produced from a material containing a polyhydroxyalkanoate (hereinafter also referred to as "PHA"): (1) has excellent heat resistance characteristics, and therefore can be employed to prevent leaking during packing of methyl methacrylate, which emits heat during curing, and can be used as a leak-preventive material during packing of any of the bone cements used in the past, including calcium phosphate and other such osteoconductive bone cements; (2) has exceptionally good elongation, allowing it to elongate in accordance with the injection of the bone cement paste, and the bone cement can therefore be packed into every corner of asperities within the medullary cavity; and (3) has excellent biodegradability in the body as compared with past biodegradable materials such as poly (lactic acid) and the like, and therefore when an osteoconductive bone cement such as calcium phosphate or the like is used, the bone and the bone cement may rapidly come into contact, promoting regeneration of the bone.

The present invention was perfected on the basis of the further discovery that by producing the intramedullary rod from a biodegradable material, and employing a combination of the aforedescribed three-dimensional structure, the intramedullary rod produced from a biodegradable material, and bone cement, there can be obtained a filler material affording strength sufficient to withstand stress created by bending, pulling, compression, and the like, without the use of metal.

Specifically, it is an object of the present invention to provide (1) a three-dimensional structure produced from a PHA-containing material, (2) an intramedullary rod produced from a biodegradable material, and (3) a kit for preparation of a filler material, including a three-dimensional structure produced from a PHA-containing material, an intramedullary rod produced from a biodegradable material, and bone cement material.

Means to Solve the Problems

As shown below, the present invention relates to (1) a three-dimensional structure produced from a PHA-containing material, (2) an intramedullary rod produced from a biodegradable material, and (3) a kit for preparation of a filler material, including a three-dimensional structure produced from a PHA-containing material, an intramedullary rod produced from a biodegradable material, and bone cement material.

(1) A three-dimensional structure produced from a material containing a polyhydroxyalkanoate.
(2) The three-dimensional structure according to (1) above, wherein the three-dimensional structure is designed to prevent bone cement from leaking during injection of the bone cement into a bone fracture site.
(3) The three-dimensional structure according to (1) or (2) above, wherein the polyhydroxyalkanoate is a copolymer of at least two substances selected from 3-hydroxybutyric acid, 3-hydroxyvaleric acid, and 4-hydroxybutyric acid.
(4) The three-dimensional structure according to any of (1) to (3) above, wherein the three-dimensional structure is obtained by depositing fibers measuring 1-100 μm in diameter produced from the material containing a polyhydroxyalkanoate.
(5) The three-dimensional structure according to any of (1) to (4) above, wherein the three-dimensional structure extends by 200% or more.
(6) A kit for preparation of a bone filler, including the three-dimensional structure according to any of (1) to (5) above, and a bone cement.
(7) A kit for preparation of a bone filler, including the three-dimensional structure according to any of (1) to (5) above, an intramedullary rod produced from a biodegradable material, and a bone cement.
(8) The kit for preparation of a bone filler according to (7) above, wherein the intramedullary rod is a cylindrically shaped object having a mesh opening structure of a size permitting bone cement to be exuded.
(9) The kit for preparation of a bone filler according to (7) or (8) above, wherein the bone cement is selected from methyl methacrylate or an osteoconductive material.
(10) An intramedullary rod produced from a biodegradable material.
(11) The intramedullary rod according to (10) above, wherein the intramedullary rod is a cylindrically shaped object having a mesh opening structure of a size permitting bone cement to be exuded.

Advantageous Effects of the Invention

The three-dimensional structure produced from a PHA-containing material according to the present invention has excellent heat resistance characteristics, and therefore can be employed to prevent leaking during packing of methyl methacrylate which emits heat during curing, and can be used as a leak-preventive material during packing of any of the bone cements used in the past, including calcium phosphate and other such osteoconductive bone cements. Additionally, because the three-dimensional structure of the present invention has exceptionally good elongation, it can elongate in accordance with the injection of the bone cement paste, and the bone cement can therefore be packed into every corner of asperities within the medullary cavity. Furthermore, due to the excellent biodegradability in the body as compared with previous biodegradable materials such as poly(lactic acid) and the like, when an osteoconductive bone cement such as calcium phosphate or the like is used, the bone and the bone cement may rapidly come into contact, promoting regeneration of the bone.

By employing the combination according to the present invention, of a three-dimensional structure produced from a PHA-containing material, an intramedullary rod produced from a biodegradable material, and bone cement material, the bending strength of the bone cement is dramatically improved. Consequently, a calcium phosphate-based bone cement, which being osteoconductive is favorable for use as a filler at a bone fracture site, but weak with respect to bending, making it difficult to use alone, can now be used as the filler, making it possible to utilize an osteoconductive bone cement, even at bone fracture sites that in the past were packed with high-strength methyl methacrylate.

Additionally, by employing the intramedullary rod produced from the biodegradable material of the present invention, there is no risk of injury to biological tissue if re-fracture should occur, in contrast to past metal products.

DESCRIPTION OF THE EMBODIMENTS

Figure 1:
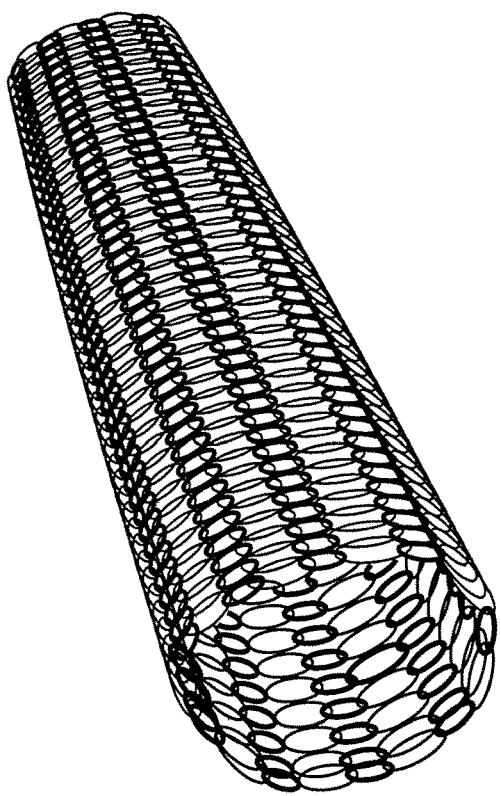
FIG. 1 is a photograph substituting for a drawing, showing a photograph of this intramedullary rod.

Following is a detailed description of (1) a three-dimensional structure produced from a PHA-containing material, (2) an intramedullary rod produced from a biodegradable material, and (3) a bone-filler material, including a three-dimensional structure produced from a PHA-containing material, an intramedullary rod produced from a biodegradable material, and bone cement material.

Firstly, the three-dimensional structure of the present invention refers to deposited fibers of a PHA-containing material (herein denoted as "PHA fibers"), such as a nonwoven fabric, floc, or the like, which have not been woven like knit fabric.

The PHA employed to produce the three-dimensional structure of the present invention is a known biodegradable material, in which the constituent monomers are alkanoic acids having an added hydroxyl group, the monomers forming a polymer through ester bonding.

As typical monomers for constituting the PHA there may be cited 3-hydroxybutyric acid (3HB), 3-hydroxyvaleric acid (3HV), 4-hydroxybutyric acid (4HB), 3-hydroxypropionic acid (3HP), 3-hydroxyhexanoic acid (3HH), 3-hydroxyoctanoic acid (3HO), 3-hydroxydecanoic acid (3HD), 4-hydroxyvaleric acid (4HV), and the like. The polymer may be formed using these monomers alone, or in combinations of two or more, with either random or block copolymers being acceptable. P(3HB), which is an example of a polymer produced from a single monomer, has a melting point of 170-180° C., which is sufficient to withstand the heat emitted when methyl methacrylate cures. On the other hand, P(3HB) is highly crystalline, rigid, and brittle, and is therefore preferably made pliable so as to be able to closely contact every corner of asperities in the medullary cavity, and is preferably employed in the form of a copolymer such as P(3HB-co-3HV), P(3HB-co-4HB), P(3HB-co-4HV), or the like. Pliability may be imparted by adjusting, as appropriate, the ratio of the monomers constituting the copolymer.

While pliability may be obtained through copolymerization, the glass transition point of the copolymers decreases. Therefore, the copolymer ratio should be adjusted with reference to pliability and heat resistance; e.g., with P(3HB-co-3HV), the proportion of 3HV in the copolymer is preferably 5-50%, and more preferably 10-20% (molar ratio). In the case of P(3HB-co-4HB), the proportion of 4HB in the copolymer is preferably 5-50%, and more preferably 10-20% (molar ratio). PHA of such ratios may be manufactured by known methods; alternatively, commercially available products such as PHA-18 (3HB:4HB=82:18) from G5 Japan K.K. may be employed.

The molecular weight is preferably 50-3,000 kDa, more preferably 300-1,500 kDa. A molecular weight of less than 50 kDa results in severe degradability, whereas a molecular weight of more than 3,000 kDa is associated with an undesirably long degradation time of several years or more.

The three-dimensional structure of the present invention may be produced from the aforedescribed PHA only, though glycolic acid or the like may be additionally added.

The three-dimensional structure is produced by dissolving PHA material in a solvent such as chloroform, dichloromethane, or the like; and employing a solution or slurry adjusted to a viscosity such that PHA fibers can be produced (herein denoted as "PHA solution"), to carry out spinning by electrospinning. Electrospinning is a method in which a positive high voltage is applied to the PHA solution, and the PHA solution is transformed into PHA fibers in the course of spraying the PHA solution from nozzles onto a negatively charged collector. The resulting three-dimensional structure can be adjusted when the PHA solution is to be sprayed from the nozzles towards the collector by electing whether or not to perform the process under a forced air stream, or by adjusting the intensity of the forced air stream. When the PHA solution is sprayed in the absence of a forced air stream, the emerging PHA solution is drawn out into fibers by the power of the magnetic field, and the PHA fibers are deposited on the collector. At this time, when the PHA fibers deposited on the collector contain solvent, the PHA fibers soften and fold over to become deposited two-dimensionally, producing a nonwoven fabric.

In contrast to this, when spraying is performed under a forced air stream, evaporation of the solvent is accelerated, and the PHA fibers can reach the collector in a state in which substantially no solvent is contained. Therefore, because the PHA fibers deposited on the collector contain substantially no solvent, the fiber shape can be maintained without softening, and the PHA fibers become deposited three-dimensionally, without folding over. The less adhesion there is among fibers, the greater is the ability of the three-dimensional structure obtained thereby to elongate, and therefore during production of the three-dimensional structure, the flow of forced air should be adjusted so as to give the desired amount of elongation.

Besides the aforedescribed method, electrospinning may be performed while the collector is submerged in a container filled with ethanol or the like. With this method, the PHA fibers can be guided into the ethanol or the like, during which process the solvent elutes out into the ethanol or the like, so that the fibers no longer adhere to one another. In the process of recovery of the floating fibers, the fibers naturally become entangled with one another, and a floc material can be obtained. Stirring or the like may be employed concomitantly to facilitate fiber entanglement.

It is necessary for the three-dimensional structure produced from the material containing PHA to be able to expand or contract, under the pressure created during injection of the bone cement, without the bone cement leaking from gaps in the three-dimensional structure; and moreover for the bone cement to not leak out even after contacting the inner face of the bone. The bone cement is typically injected into the medullary cavity through a syringe; while the pressure produced by the syringe during the process will differ depending on the material and the viscosity of the bone cement, about 2-4 MPa will be required. The bone cement injected from the tip of the syringe into the interior of the intramedullary rod, discussed below, gives rise to elongation of the three-dimensional structure through the spaces in the intramedullary rod, with the three-dimensional structure ultimately elongating to the point of abutting the bone surface of the asperities of the medullary cavity, and once the bone cement is packed into the medullary cavity leaving no gaps, the pressure of the bone cement pressing against the three-dimensional structure rises to a pressure approximating the pushing pressure of the syringe. Consequently, the three-dimensional structure produced from a material containing PHA of the present invention will preferably not leak bone cement, even when subjected to pressure of at least about 2-4 MPa. In order to have characteristics such as that described above, the three-dimensional structure must dilate without any rise in internal pressure despite the increasing injected amount of bone cement, i.e., for the intrinsic amount of elongation of the three-dimensional structure to be at least greater than the amount of elongation required during packing of the bone cement into the medullary cavity. Specifically, elongation of about 200% or more is preferred.

Of the bone cements to be discussed later, in cases in which, for example, an osteoconductive calcium phosphate-based bone cement is employed, because the calcium phosphate or the like contributes to regeneration, it is preferable for the material to contact the inner face of the bone. Consequently, it is preferable for the three-dimensional structure of the present invention to have dimensions such that, while particles of bone cement do not leak out even in a state in which the three-dimensional structure into which the bone cement has been injected abuts the medullary cavity interior, the particles of bone cement are exposed at the surface of the three-dimensional structure.

In order for the three-dimensional structure to be endowed with characteristics such as those described above, the diametrical size of the PHA fibers should be adjusted, albeit with respect to the particle size and viscosity of the bone cement. If the PHA fibers constituting the three-dimensional structure are too large in diameter, the dimensions of the gaps in the three-dimensional structure obtained therefrom will be too large, posing a risk that bone cement particles will leak out. If the PHA fibers constituting the three-dimensional structure are too small in diameter, the dimensions of the gaps in the three-dimensional structure obtained therefrom will be too small, and due to the viscosity of the bone cement paste, the bone cement particles will fail to be exposed at the surface of the three-dimensional structure. Consequently, while dependent upon the particle size and viscosity of the bone cement being employed, the average diameter of the PHA fibers is preferably about 1-100 μm, more preferably about 5-20 μm.

The PHA fibers of the present invention are drawn out into fibers by the power of an electrical field on the emerging solution or slurry by an electrospinning process, and therefore the average diameter can be controlled through adjustment of the viscosity of the solution or slurry. Increasing the viscosity will result in a thicker average diameter being obtained, while reducing the viscosity will result in a thinner average diameter being obtained. In order to achieve the aforedescribed average diameter, appropriate adjustments should be made while giving consideration to the concentration of the solution and the molecular weight of the material, as well as the dielectric constant of the solution and the like. Apart from electrospinning processes, the PHA fibers of the present invention can be obtained, for example, by injecting a PHA solution or slurry from a syringe into a stirred ampiphilic liquid such as methanol, ethanol, or the like, to draw out fibers by stirring. The diameter of the PHA fibers can be controlled by changing the force at which the PHA solution or slurry is drawn out, through adjustment of the viscosity of the PHA solution or slurry and of the intensity level of the stirring. Electrospinning may be suitable in cases of production of small-diameter PHA fibers, whereas a method of injecting a PHA solution or slurry from a syringe into a stirred ampiphilic liquid such as methanol, ethanol, or the like may be suitable in cases of production of large-diameter PHA fibers, appropriate selection being made according to the desired diameter.

There are no particular limitations as to the bone cement employed in the present invention as long as the bone cement is capable of being injected into a bone fracture site and cured; any of materials of various compositions employed in the past for these sorts of applications can be used. For example, bone cement materials having polymethyl methacrylate as the principal component (for example, bone cement materials containing, besides polymethyl methacrylate, barium powder, methyl methacrylate (monomers), and the like) can be used.

Apart from polymethyl methacrylate, there can be cited calcium phosphate based cement materials. Calcium phosphate is a constituent component of bone, and these bone cements are preferred for their exceptional osteoconductivity and biocompatibility. Moreover, calcium phosphate based cement materials, when employed as a constituent material of a bone filler preparation kit, can be stored in solid form (typically powder form) until the curing process is carried out, and therefore are preferable for the purpose of constructing the kit of the present invention.

The calcium phosphate based cement materials may contain calcium phosphates of various chemical composition ratios. As suitable materials, there can be cited hydroxyapatite ($Ca_{10}(PO_4)_6(OH)_2$), or compounds capable of forming hydroxyapatite through hydrolysis. For example, there may be cited mixtures containing α-type tricalcium phosphate (α-$Ca_3(PO_4)_2$ as the principal component, and other calcium phosphate compounds as auxiliary components. For example, α-type tricalcium phosphate to which has been added hydroxyapatite, β-type tricalcium phosphate (β-$Ca_3(PO_4)_2$, tetracalcium phosphate ($Ca_4(PO_4)_2O$), calcium hydrogen phosphate ($CaHPO_4.2H_2O$), or the like may be cited. Other calcium phosphate compounds besides the examples cited here may be used, with no particular limitations, provided that the combination of compounds used is a combination above to form a hydroxyapatite [or] other calcium phosphate based cement base material (cured article).

Compounds besides the calcium phosphate compound representing the principal component may be contained, provided that a calcium phosphate based cement base material (cured article) is obtained. For example, compounds in which a portion of the Ca in the calcium phosphate compound is substituted with other elements (e.g., Sr, Ba, Mg, Fe, Al, Na, K, H) may be contained. Alternatively, compounds in which a portion of the $PO_4$ is substituted with other acid components (e.g., $CO_3$, $BO_3$, $SO_4$, $SiO_4$) may be contained.

The aforedescribed calcium phosphate-based bone cements have osteoconductivity and biocompatibility, and are preferred as materials for fillers of bone fracture sites; however, due to their brittleness, in the past, these were not employed by themselves to join bone fractures of long bones. However, by concomitantly employing the three-dimensional structure produced from a material containing PHA, and the intramedullary rod produced from a biodegradable material, according to the present invention, calcium phosphate-based bone cements can be employed to treat bone fractures of long bones, which are subjected to relatively more stress such as bending, pulling, and compression, than are other bones.

The bone cement employed in the present invention may be produced through appropriate preparation of the aforedescribed starting materials, or a commercially available product may be used. For example, bone cements containing methyl methacrylate as the principal component are commercially available under trade names such as Surgical Simplex (from Stryker Japan K.K.), Ostron II (from GC K.K.), while osteoconductive bone cements are commercially available under trade names such as Biopex-R (Advanced Full Set) (HOYA Corp.), Cerapaste (made by NGK Spark Plug Co. Ltd., sold by Kobayshi Medical), and Primafix (made by Nihon MDM Inc.).

As shown in FIG. 1, the intramedullary rod employed in the present invention takes the form of a cylinder in which a biodegradable material is woven into a mesh structure, the structure being such that when bone cement is injected into the cavity of the cylinder, the bone cement migrates out from the intramedullary rod through the gaps in the mesh. The diameter and length of the intramedullary rod should be smaller than the diameter of the cavity of the bone at the bone fracture site being employed. Increasing the number of knit layers forming the cylinder improves the bending resistance, and therefore the number of knitting cycles may be adjusted as appropriate, giving consideration to the cavity diameter of the bone at the application site, and stresses such as bending, pulling, and compression on the bone fracture site. The size of the mesh openings may be adjusted appropriately through the spacing of the warp and woof.

As biodegradable materials employed to produce the intramedullary rod, there may be cited, as biodegradable resins, synthetic polymers such as poly(lactic acid) (PLA), poly(glycolic acid) (PGA), polyethylene glycol (PEG), polycaprolactone (PCL), or PHA polymers, or copolymers of two or more monomers selected from PLA, PGA, PEG, PCL, and PHA; or natural polymers such as fibrin, collagen, alginic acid, hyaluronic acid, chitin, chitosan, or the like.

During treatment of a bone fracture site, the three-dimensional structure produced from a PHA-containing material, the intramedullary rod produced from a biodegradable material, and the bone cement material may be employed in combination, or arranged beforehand in the form of a kit for preparation of bone filler.

Figure 2:
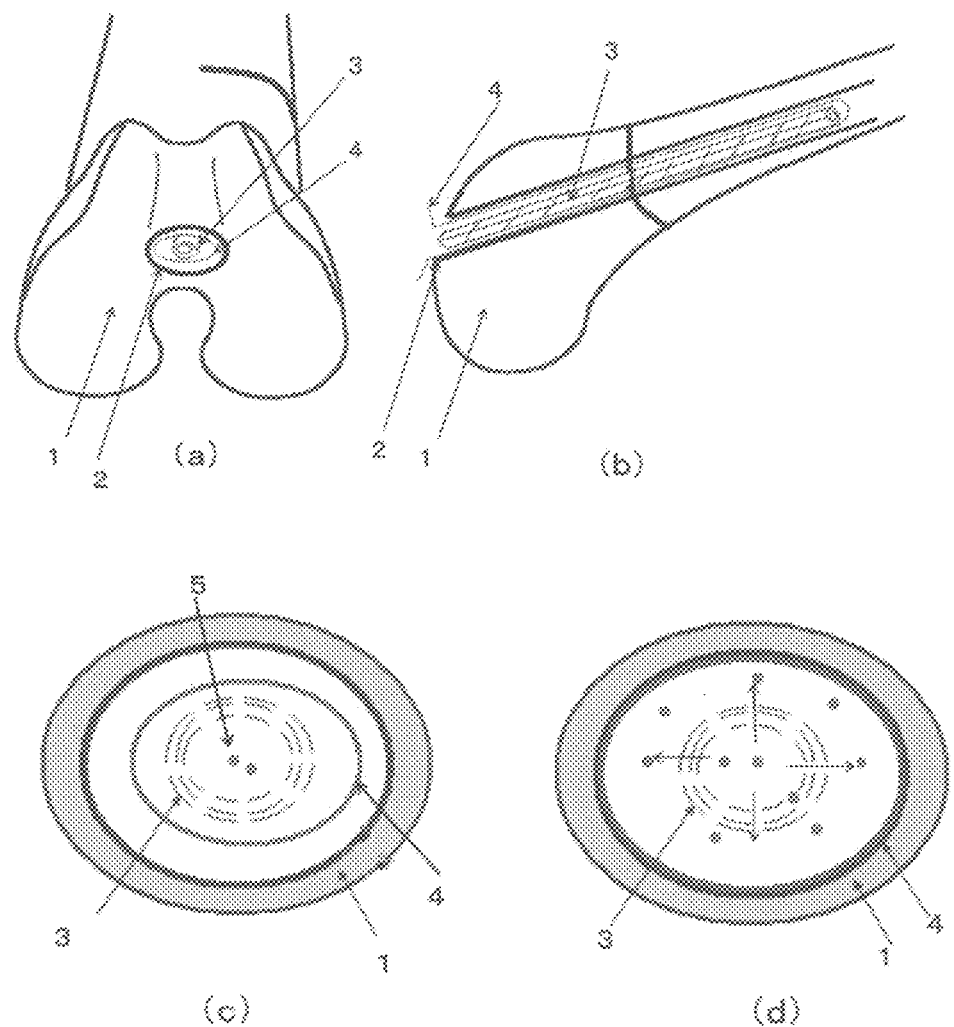
FIG. 2 is a diagram showing an example of a method for using the three-dimensional structure produced from a PHA-containing material, the intramedullary rod produced from a biodegradable material, and the bone cement material of the present invention.

FIG. 2 is a diagram showing an example of a method for using the three-dimensional structure produced from a PHA-containing material, the intramedullary rod produced from a biodegradable material, and the bone cement material. FIG. 2 (a) is a cross sectional view of the end of a long bone, (b) is a longitudinal axis cross sectional view of a long bone, (c)

is an axis-perpendicular view of a long bone prior to bone cement injection, and (d) is an axis-perpendicular view of a long bone after bone cement injection.

As shown in FIG. 2(a), firstly, a drill or the like is employed to form a small hole 2 in an end 1 of a long bone. Next, a three-dimensional structure 4 of pouch form is formed around an intramedullary rod 3, which is then inserted inside the long bone from the small hole 2 as shown in FIG. 2(b). Immediately after insertion, as shown in FIG. 2(c), the intramedullary rod 3 and the three-dimensional structure 4 do not about the inner face of the long bone 1, producing a state in which there is a gap between them. Then, when bone cement 5 is injected into the center part of the intramedullary rod 3, as shown in FIG. 2(d), the injected bone cement 5 migrates to the outside through the mesh openings of the intramedullary rod 3, and the three-dimensional structure 4, which has excellent elongation, is expanded by being pushed until abutting the inside of the long bone 1, and bone cement 5 becomes packed into all corners of the inner face of the long bone 1. In cases in which an osteoconductive calcium phosphate system is used as the bone cement 5, in a state in which the three-dimensional structure 4 abuts the inside of the long bone 1, the bone cement 5 does not leak out from the three-dimensional structure, but particles of the bone cement 5 are in a state of partial exposure at the outermost face of the three-dimensional structure. Consequently, the osteoconductive calcium phosphate directly contacts the bone, thereby promoting self-repair of the bone.

Furthermore, the PHA constituting the three-dimensional structure of the present invention has better biodegradability than other biodegradable materials. Therefore, the bone cement cures, and once there is no longer any concern of the bone cement migrating out from the bone, rapidly degrades; therefore, foreign matter is eliminated between the bone and the osteoconductive material, so that these unify, further promoting self-repair of the bone.

While the present invention is described with more specificity below in terms of certain examples, the examples are merely illustrative of the present invention, and are provided for reference to certain specific modes. While certain specific modes of the present invention are illustrated in exemplary fashion thereby, the scope of the invention disclosed herein is in no way limited or restricted thereby.

EXAMPLES

Materials Used in Examples and Comparative Examples
PHA: PHA-18 (3HB:4HB=82:18) from G5 Japan K.K. (hereinafter denoted as "PHA-18")
PLLA: LACEA (from Mitsui Chemicals Inc., Mw: 140 kDa)
PLGA: Purasorb™ PDLG (from Purac, Mw: 140 kDa, PLA:GPA=75:25
Chloroform (CHCl$_3$): special grade reagent, ≥99.0 pure, from Kishida Chemical Co., Ltd.
Calcium phosphate-based bone cement: Biopex-R (Advanced Full Set) (from HOYA K.K.)
Methyl methacrylate bone cement: Ostron II (from GC Co. Ltd.)
(Production of Three-dimensional Structure (Nonwoven Fabric))

Example 1

2 g of PHA-18 was dissolved in chloroform, bringing the PHA concentration to 6 wt %. Solution viscosity at this time was 2.8 Pa·s. 10 mL of the above solution was placed into a glass syringe barrel. A collector was set up by wrapping aluminum foil onto a grounded rotating drum. Attaching a 22 G syringe needle and applying a voltage of 10 kV so as to positively charge the needle section, the solution was ejected at 0.35 mm/min and spun onto the collector to produce a nonwoven fabric 0.1 mm thick. The fiber diameter was approximately 10 μm. The melting point and glass transition temperature of the nonwoven fabric so obtained were measured with differential scanning calorimetry; the melting point was 130° C. and the glass transition temperature was −20° C.

Comparative Example 1

2 g of PLLA was dissolved in chloroform, adding methanol (special grade from Wako Pure Chemical Industries Ltd.) to bring the PLLA:chloroform:methanol weight ratio to 10:67.5:22.5. Solution viscosity at this time was 0.5 Pa·s. 10 mL of the above solution was placed into a glass syringe barrel. A collector was set up by wrapping aluminum foil onto a grounded rotating drum. Attaching a 22 G syringe needle and applying a voltage of 15 kV so as to positively charge the needle section, the solution was ejected at 0.35 mm/min and spun onto the collector to produce a nonwoven fabric 0.1 mm thick. The fiber diameter was approximately 2 μm. The melting point and glass transition temperature of the nonwoven fabric so obtained were measured with differential scanning calorimetry; the melting point was 170° C. and the glass transition temperature was 56° C.

Comparative Example 2

2 g of PLLA was dissolved in chloroform, bringing the PLLA concentration to 13 wt %. Solution viscosity at this time was 3 Pa·s. 10 mL of the above solution was placed into a glass syringe barrel. A collector was set up by wrapping aluminum foil onto a grounded rotating drum. Attaching a 22 G syringe needle and applying a voltage of 15 kV so as to positively charge the needle section, the solution was ejected at 0.35 mm/min and spun onto the collector to produce a nonwoven fabric 0.1 mm thick. The fiber diameter was approximately 10 μm. The melting point and glass transition temperature of the nonwoven fabric so obtained were measured with differential scanning calorimetry; the melting point was 170° C. and the glass transition temperature was 56° C.

Figure 3:
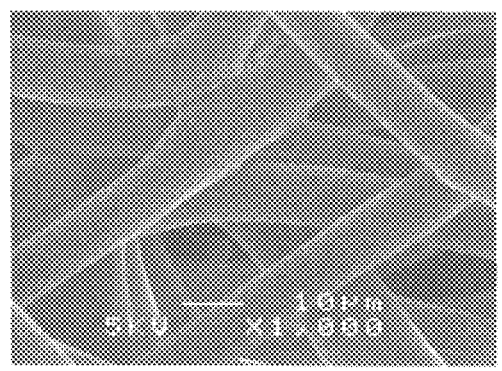
FIG. 3 shows photographs substituting for drawings, showing SEM photographs of (a) a nonwoven fabric of PHA-18 (10 µm) produced in Example 1, (b) a nonwoven fabric of PLLA (2µm) produced in Comparative Example 1, and (c) a nonwoven fabric of PLLA (10 µm) produced in Comparative Example 2.
Figure 3:
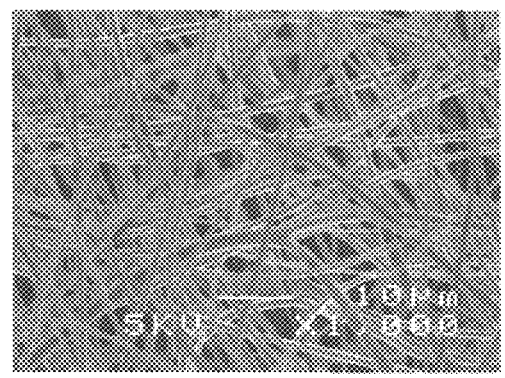
Figure 3:
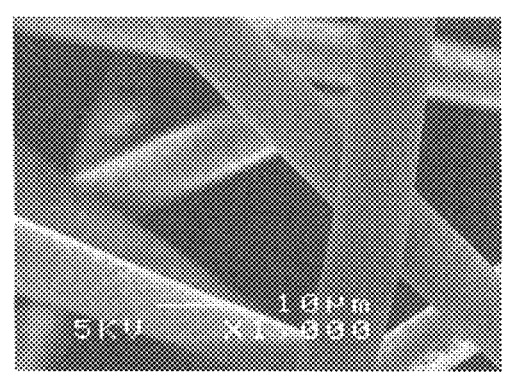

FIG. 3(a) is an SEM photograph of the nonwoven fabric of PHA-18 (10 μm) produced in Example 1, (b) an SEM photograph of the nonwoven fabric of PLLA (2 μm) produced in Comparative Example 1, and (c) an SEM photograph of the nonwoven fabric of PLLA (10 μm) produced in Comparative Example 2.

Figure 4:
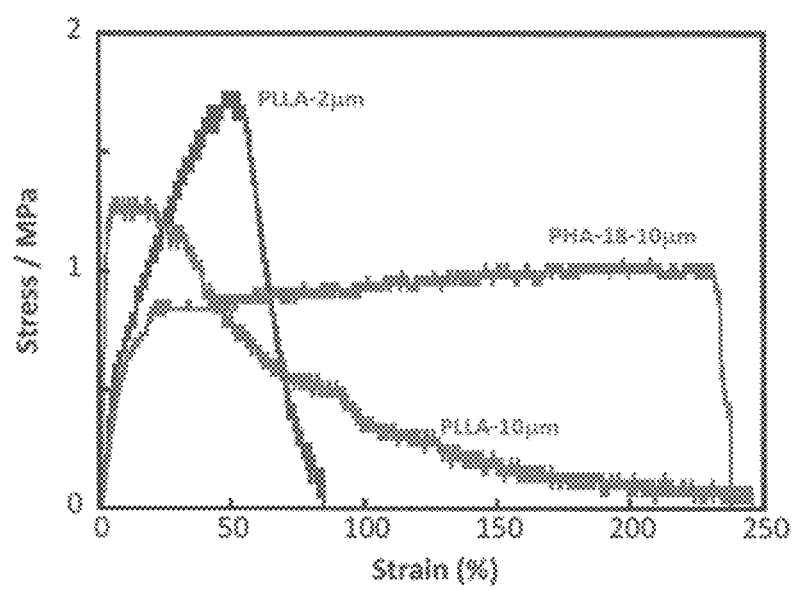
FIG. 4 is a graph showing stress-strain curves for the nonwoven fabric of PHA-18 (10 µm) produced in Example 1, the nonwoven fabric of PLLA (2 µm) produced in Comparative Example 1, and the nonwoven fabric of PLLA (10 µm) produced in Comparative Example 2.

FIG. 4 is a graph showing stress-strain curves for the nonwoven fabrics produced in Example 1 and Comparative Examples 1 and 2 were cut into 20 mm (length)×5 mm (width)×approximately 0.1 mm (thickness) pieces and tested in the air at room temperature under a 5 mm/min crosshead speed. As shown in FIG. 4, with the 2 μm diameter PLLA, the fibers began to break once the amount of strain exceeded about 50%. The 2 μm diameter PLLA exhibited high maximum stress, which is attributed to the presence of dense sections in which the fibers are stuck together. With the 10 μm diameter PLLA, the fibers began to break once the amount of strain exceeded about 20%. On the other hand, with the 10 μm diameter PHA-18, there was no change in stress from the 20%-230% level, and the fibers extended with no breakage whatsoever, demonstrating excellent extensibility.

(Production of Three-dimensional Structure (Nonwoven Fabric))

Example 2

4 g of PHA-18L was dissolved in chloroform, bringing the PHA concentration to 6 wt %. Solution viscosity at this time was 2.8 Pa·s. 10 mL of the above solution was placed into a glass syringe barrel. 1.5 L of ethanol was placed in 400×200×40 mm plastic tray, in the bottom of which was submerged a grounded stainless steel plate 10 mm in diameter. Attaching a 22 G syringe needle and applying a voltage of 10 kV so as to positively charge the needle section, the solution was ejected at 0.35 mm/min and spun into the ethanol. The floating fibers were recovered with tweezers, placed on filter paper, and dried at room temperature. The fiber diameter was approximately 10 μm. The melting point and glass transition temperature of the flocculent substance so obtained were measured with differential scanning calorimetry; the melting point was 130° C. and the glass transition temperature was −20° C.

Comparative Example 3

4 g of PLLA was dissolved in chloroform, bringing the PLLA concentration to 10 wt %. Solution viscosity at this time was 2.5 Pa·s. 10 mL of the above solution was placed into a glass syringe barrel. 1.5 L of ethanol was placed in 400×200×40 mm plastic tray, in the bottom of which was submerged a grounded stainless steel plate 10 mm in diameter. Attaching a 22 G syringe needle and applying a voltage of 20 kV so as to positively charge the needle section, the solution was ejected at 0.35 mm/min and spun into the ethanol. The floating fibers were recovered with tweezers, placed on filter paper, and dried at room temperature. The fiber diameter was approximately 10 μm. The melting point and glass transition temperature of the flocculent substance so obtained were measured with differential scanning calorimetry; the melting point was 170° C. and the glass transition temperature was 56° C.

Comparative Example 4

4 g of PLGA was dissolved in chloroform, bringing the PLGA concentration to 16 wt %. Solution viscosity at this time was 3 Pa·s. 10 mL of the above solution was placed into a glass syringe barrel. 1.5 L of ethanol was placed in 400×200×40 mm plastic tray, in the bottom of which was submerged a grounded stainless steel plate 10 mm in diameter. Attaching a 22 G syringe needle and applying a voltage of 15 kV so as to positively charge the needle section, the solution was ejected at 0.35 mm/min and spun into the ethanol. The floating fibers were recovered with tweezers, placed on filter paper, and dried at room temperature. The fiber diameter was approximately 10 μm. The melting point and glass transition temperature of the flocculent substance so obtained were measured with differential scanning calorimetry; the melting point was 170° C. and the glass transition temperature was 50° C.

Figure 5:
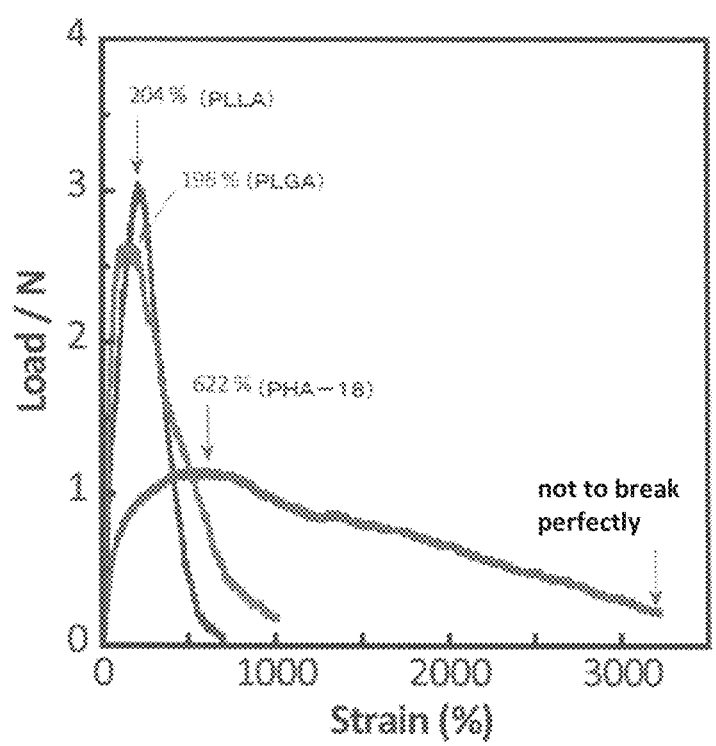
FIG. 5 is a graph showing load-strain curves for a floc material of PHA-18 produced in Example 2, a floc material of PLLA produced in Comparative Example 3, and a floc material of PLGA produced in Comparative Example 4.

The floc materials produced in Example 2 and Comparative Examples 3 and 4 were cut into 20 mm (length)×5 mm (width)×approximately 10 mm (thickness) pieces. Because the materials produced in Example 2 and Comparative Examples 3 and 4 were in a fluffy floc state, the thickness is an approximate dimension. However, each of the materials produced had weight of about 1.8 g. FIG. 5 shows load-strain curves for these materials when tested in the air at room temperature under conditions of a 5 mm/min crosshead speed. As shown in FIG. 5, after a load was applied to the PLLA and PLGA up to an amount of strain of about 200%, the fibers suddenly broke. On the graph, the floc materials appear to extend up 500-1,000%, but the fibers themselves did not stretch appreciably, and therefore fiber breakage progressed rapidly. With the PHA-18, on the other hand, after extending up to 622% with no breakage whatsoever, fiber breakage proceeded gradually. However, while some fibers broke at 622% and above, as shown in FIG. 5, the curve observed when load was applied to the PHA-18 floc material was gentle. From this data, it is clear that the number of broken fibers was not very great, and that the fibers continued to extend, thus demonstrating that a floc material produced from a PHA-containing material has better extension characteristics than do floc materials produced from PLLA or PLGA, (Injection Test of Calcium Phosphate-based Bone Cement)

Example 3

A silicone resin was injected into a glass vial having a bore size of 15 mm and length of 50 mm, and was cured while the vial was tilted, producing a random geometry model in which the resin was cured in such a way as to slope towards one end of the cap from the entire bottom face of the vial. Next, a pouch was made from the nonwoven fabric produced in the aforedescribed Example 1, and this was attached to the tip of an injection syringe in a Biopex-R (Advanced Full Set), and secured by tying at the base with thread. With regard to the mixing method and the packing method, a Biopex paste was prepared according to the accompanying manual, except for using a 6 mL set with 4.0 mL of liquid. Next, the injection syringe with the nonwoven fabric attached was inserted into the random geometry model prepared in the above manner, and the prepared Biopex was injected using the injector included in the set.

Comparative Example 5

The same test as in Example 3 was carried out, except for employing the PLLA nonwoven fabric prepared in the aforedescribed Comparative Example 2.

Figure 6:
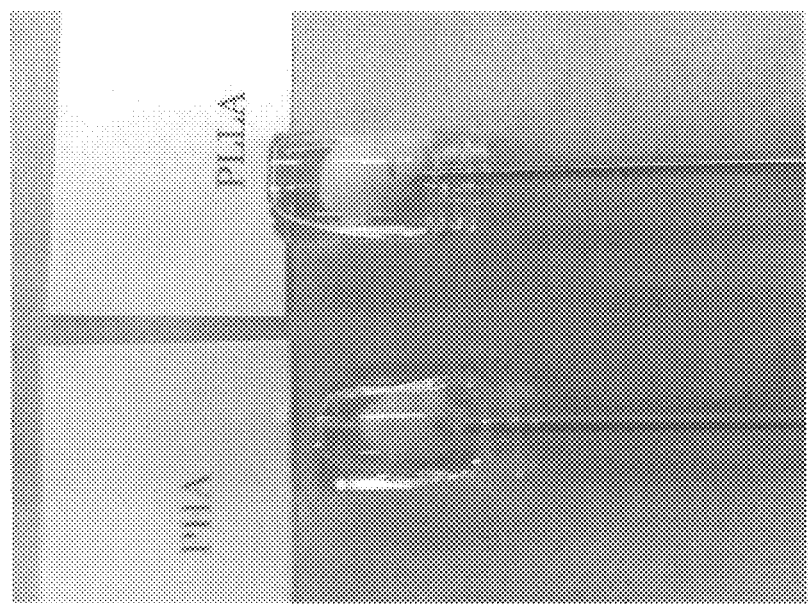
FIG. 6 is a photograph substituting for a drawing, showing injection syringes with pouches of nonwoven fabric attached thereto, in a state of being inserted into a random geometry model produced in glass vials, prior to injection of Biopex in Example 3 and Comparative Example 5.

FIG. 6 is a photograph showing injection syringes with pouches of nonwoven fabric attached thereto, in a state of being inserted into a random geometry model produced in glass vials, prior to injection of Biopex in Example 3 and Comparative Example 5.

Figure 7:
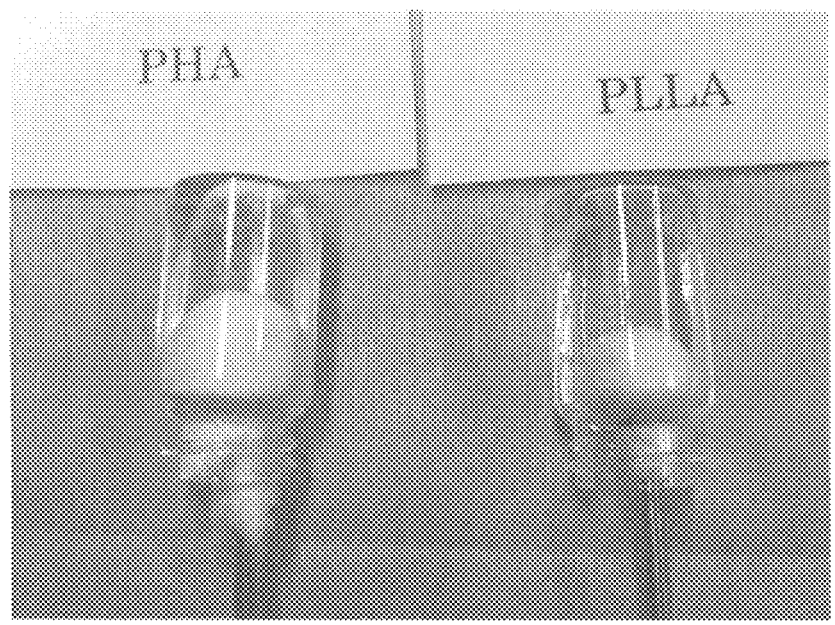
FIG. 7 is a photograph substituting for a drawing, showing a state during injection of Biopex into random geometry models produced in glass vials from the distal end of syringes with pouches of nonwoven fabric attached thereto in Example 3 and Comparative Example 5.

FIG. 7 is a photograph showing a state during injection of the Biopex in Example 3 and Comparative Example 5, in which the nonwoven fabric produced from PHA in Example 3 has elongated like a rubber balloon according to the injected amount of Biopex. In the case of the nonwoven fabric produced from PLLA in Comparative Example 5, on the other hand, the cement exuded from the surface of the pouch, forming small clumps.

Figure 8:
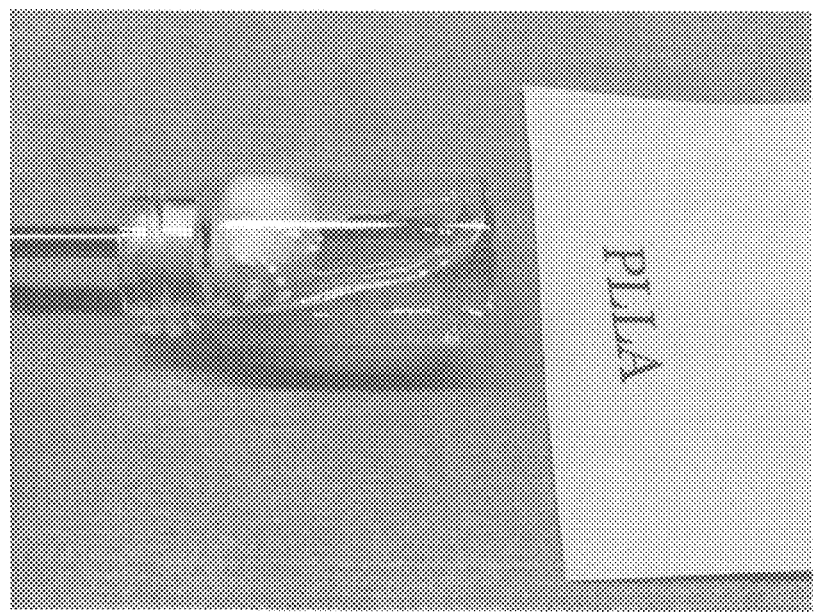
FIG. 8 is a photograph substituting for a drawing, showing an enlargement taken in a lateral direction in a state during injection of Biopex in Comparative Example 5.

FIG. 8 is an enlargement taken in a lateral direction in a state during injection of Biopex in Comparative Example 5; as is clear from the photograph, due to the poor elongation of the nonwoven fabric produced from PLLA, once elongated above a given level, the material could elongate no further despite increasing the injection pressure of the Biopex, and the Biopex was exuded through gaps in the nonwoven fabric.

Figure 9:
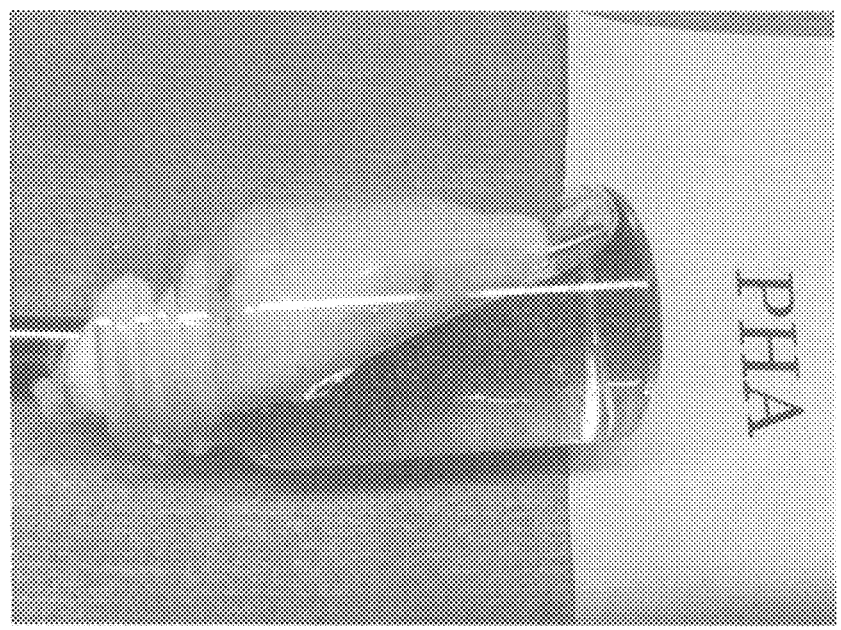
FIG. 9 is a photograph substituting for a drawing, showing an enlargement taken in a lateral direction in a state during injection of Biopex in Example 3.

In contrast to this, the nonwoven fabric produced from PHA had ample elongation, and as shown in FIG. 9, elongated as the Biopex was injected, demonstrating that even at an insertion site of random geometry, the material could extend in such a way as to fill in the gaps along the shape.

(Injection Test of Methyl Methacrylate-based Bone Cement)

Example 4

A pouch of the floc material produced in the aforedescribed Example 2 was attached to the tip of the injection syringe from the Ostron II set, and secured by tying at the base with thread. With regard to the mixing method and the packing method, a methyl methacrylate paste was prepared according to the accompanying manual, except for tinting it to pink color. Next, using the injector included in the set, the prepared methyl methacrylate paste was injected into the pouch of floc material.

Comparative Example 6

The same test as in Example 4 was carried out, except for employing the PLLA floc material prepared in the aforedescribed Comparative Example 3.

Figure 10:
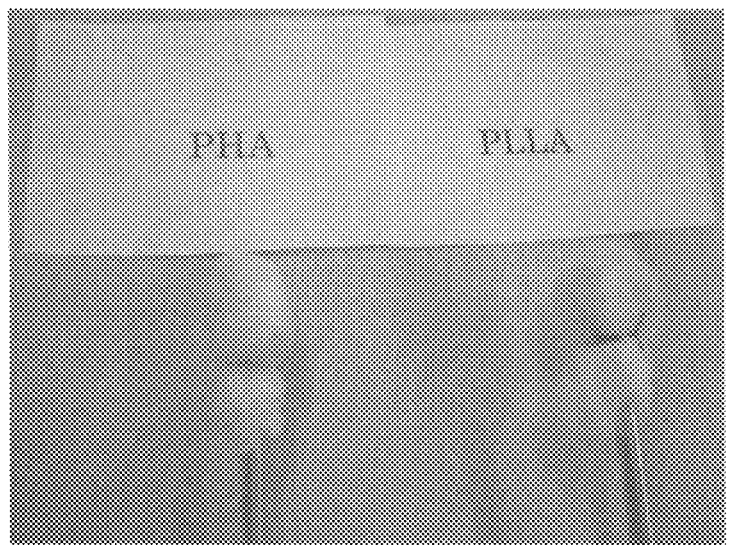
FIG. 10 shows photographs substituting for drawings, showing injection of a methyl methacrylate bone cement, taken after 20 minutes had elapsed in Example 4 and Comparative Example 6.

FIG. 10 shows photographs of injection of the methyl methacrylate bone cement, taken after 20 minutes had elapsed.

It is clear from FIG. 10 that with the floc material produced from PHA, substantially no coloration was discernible from the outside. With the floc material produced from PLLA on the other hand, there was a discernible change in color, as compared to the floc material produced from PHA. This is attributed to emission of heat during curing of the methyl methacrylate, which caused the reaction between the methyl methacrylate-based bone cement and the floc material produced from PLLA to proceed to a further extent as compared with the floc material produced from PHA, giving rise to disturbance in the fiber structure. From the above results, it was demonstrated that the floc material produced from PHA of the present invention has a leak-preventing effect, even with methyl methacrylate-based bone cements which emit heat during curing.

(Production of Biodegradable Intramedullary Rod)

Example 5

Firstly, using a tubular knitting machine, a tube of PLLA yarn was produced. A Marusan tabletop model tubular knitting machine CK-N (Marui Textile Machinery Co. Ltd.) was used as the tubular knitting machine. Using 0.2 mm-diameter monofilament was as the PLLA yarn, and knitting a flat knit with 12 knitting needles, a cylindrical tube about 5 mm in diameter was produced.

Next, the produced tube was cut to lengths of 150 mm, which were stacked in three layers, inserting a Teflon tube 4 mm in diameter inside. Then, in order to solvent-weld together the three stacked layers, approximately 10 mL of a solvent was applied evenly with a brush. The solvent used was a solution containing a mixture of dichloromethane (reagent special grade from Wako Pure Chemical Industries Ltd.) and methanol (Wako Class 1 from Wako Pure Chemical Industries Ltd.) in 3:1 proportions, in which PLLA had been dissolved to a proportion of 2 wt %.

After solvent welding of the three stacked layers, the inserted Teflon tube was withdrawn, and finally the ends were trimmed, to produce an intramedullary rod having an outside diameter of about 5 mm and an inside diameter of about 4 mm.

(Preparation of Animals for Bone Fragility Fracture)

In order to produce an animal model for osteoporosis accompanied by bone fragility, 20- to 25-week old female rabbits weighing approximately 3.5 kg were employed, and following the method of Castaneda et al., subsequent to ovariectomy, were for a period starting two weeks later, intramuscularly injected with a glucosteroid hormone (1.0 mg/kg/day) for a total of four weeks. Next, an electric cutter was used to produce a half-circumferential bone fracture in the distal part of the femur. To create a space for inserting the intramedullary rod, a small hole 7 mm in diameter was produced in the rabbits' distal part of the femur (the knee cartilage surface) with a drill reamer to carry out intramedullary reaming, to obtain bone fragility fracture rabbit models.

(Testing of Bone Fragility Fracture Animals)

Example 6

Animal tests were conducted using four of the bone fragility fracture rabbit models prepared as described above in (Preparation of animals for bone fragility fracture). Under full anesthesia, intramedullary rods produced in Example 5 were inserted into the femoral marrow from the aforementioned small hole. During the insertion process, the PHA nonwoven fabric produced in the aforedescribed Example 1 was wrapped around the intramedullary rod, so as to prevent the paste from leaking out during injection of the Biopex. Preparation of the Biotex was conducted in the same manner as in the aforedescribed Example 3. Following injection, the Biotex cured completely in about 15 minutes.

Comparative Example 7

Biopex was injected into four bone fragility fracture rabbit models by the same procedure as in Example 6, except that the intramedullary rods and PHA nonwoven fabric were not used.

One to two hours after surgery, the rabbits awoke from anesthesia and began to walk around. X-ray photographs were taken after one week and after one month; of the four animals of Example 6, a diphyseal bone fracture was observed in one of the animals after one week, while the other three animals were confirmed to be healing successfully with no re-fractures, even after one month, as shown in FIG. 11(a).

Figure 11:
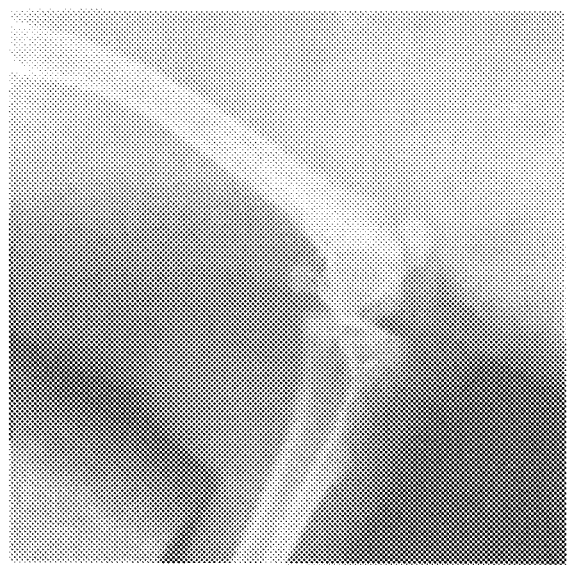
FIG. 11 shows photographs substituting for drawings, showing (a) an x-ray photograph of the rabbit treated by the procedure of Example 6, after one month, and (b) an x-ray photograph of the rabbit treated by the procedure of Comparative Example 7, after one week.
Figure 11:

With the four animals of Comparative Example 7, on the other hand, when x-ray photographs were taken after one week and after one month, of the four animals, no bone fracture was observed in one of the animals after one month, but re-fractures were confirmed in the other three animals, as shown in FIG. 11(b). From these results, the usefulness of a treatment method that concomitantly employs an intramedullary rod and Biopex is clear.

(Strength Test)

Example 7

Two acrylic pipes (outside diameter 16 mm×inside diameter 13 mm×length 35 mm) were lined up lengthwise to produce a form, which was lightly taped in advance and made cylindrical in shape. The PHA nonwoven fabric produced in the aforedescribed Example 1 was wound around an intramedullary rod (cut to 65 mm in length) produced by the same method as in Example 5, except that the outside diameter was approximately 10 mm and the inside diameter was approximately 7 mm, and this was inserted into the acrylic tubes. Next, Biopex powder was preheated in an incubator (ISUZU SKM-111S), while preheating the liquid part in a water bath (EYELA NTT-220), to 30° C. respectively. After preparing the Biopex paste by the same method as in Example 3, the paste was injected from the inside of the intramedullary rod, to produce a test piece. 10 minutes after injection, the test piece was immersed in a simulated body fluid (SBF), and held at 37° C. in an incubator (ISUZU SKM-114S).

Figure 12:
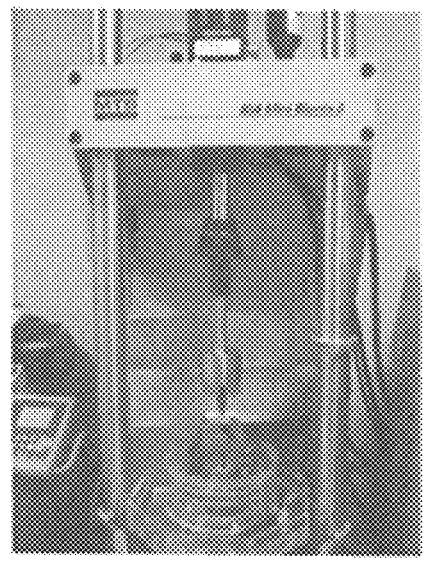
FIG. 12 shows photographs substituting for drawings, showing (a) the exterior of a three-point flexural test strength tester (MTS858 Mini Bionix II), and (b) an enlargement of the specimen and the head section.
Figure 12:
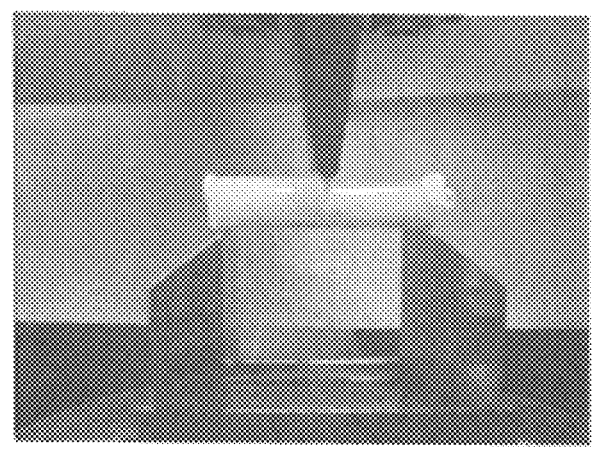

A three-point flexural strength test was conducted on test pieces prepared in the aforedescribed manner. The three-point flexural strength test was conducted with the strength tester (MTS858 Mini Bionix II) shown in FIG. 12(a), under conditions of a head speed of 0.5 mm/min. FIG. 12(b) is an enlargement of the specimen and the head section. In Example 7 and Comparative Examples 8 and 9, the number n was 5.

Comparative Example 8

A test piece was produced by the same method as in Example 7, except that an intramedullary rod was not used, and a three-point flexural test was conducted.

Comparative Example 9

A test piece was produced by the same method as in Example 7, except that an intramedullary rod and PHA nonwoven fabric were not used, and a three-point flexural test was conducted.

Figure 13:
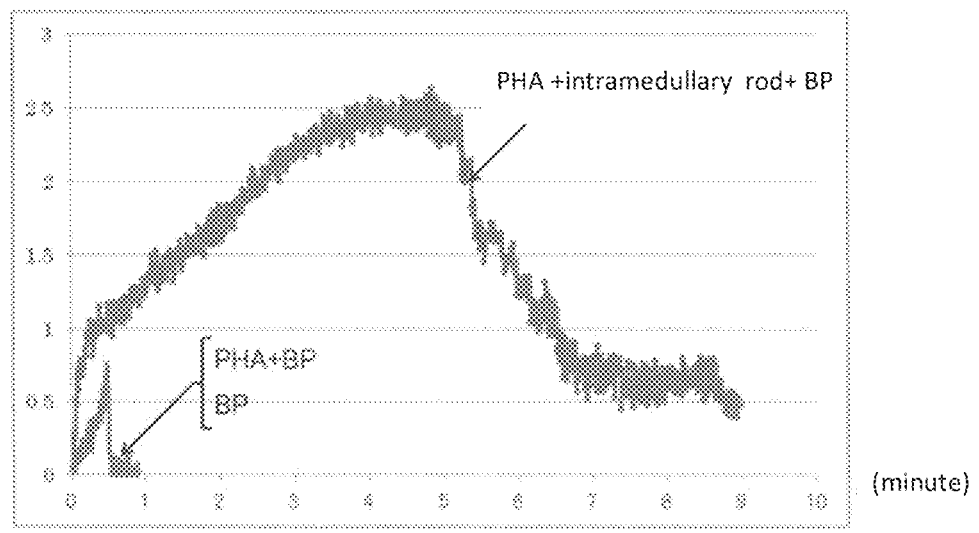
FIG. 13 is a graph showing strength test results (a strain-displacement diagram) when an intramedullary rod is used (Example 7) and when an intramedullary rod is not used (Comparative Examples 8, 9), and showing the relationship of head movement time and flexural stress values.
Figure 14:
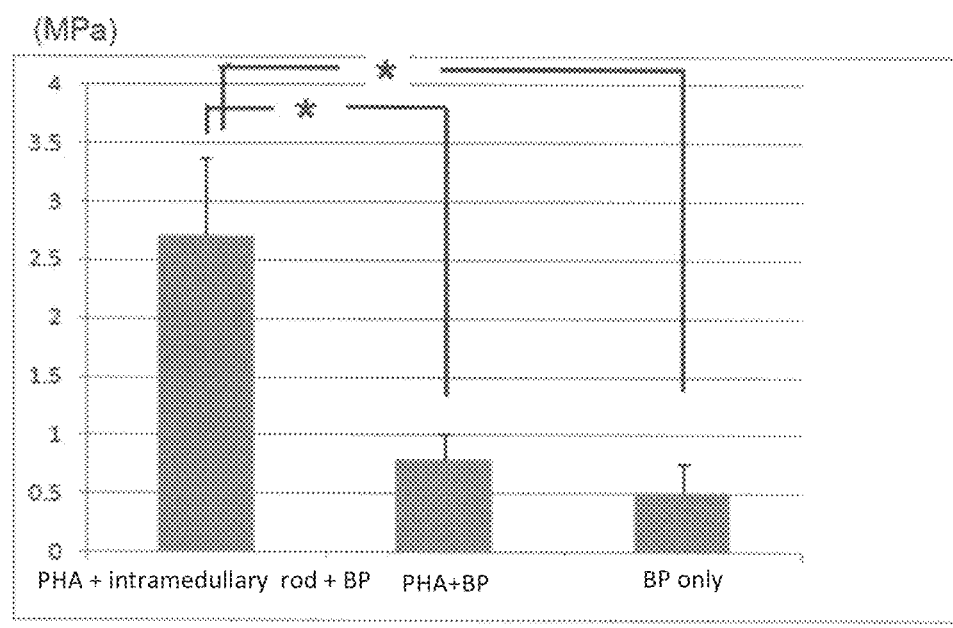
FIG. 14 is a graph showing maximum values of flexural stress when an intramedullary rod is used (Example 7) and when an intramedullary rod is not used (Comparative Examples 8, 9)
Figure 15:
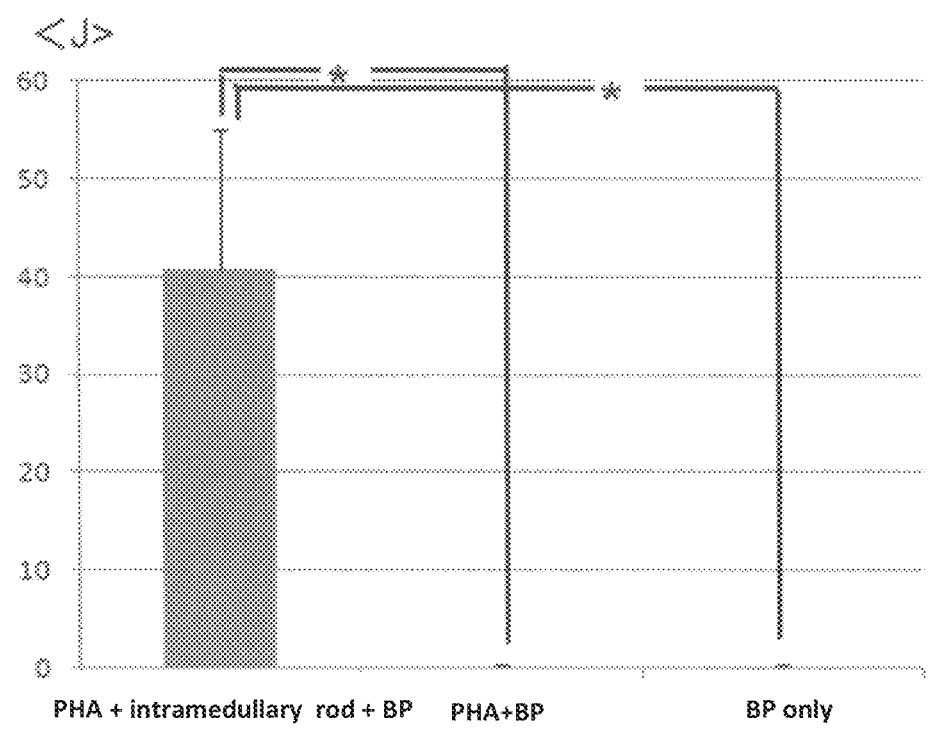
FIG. 15 is a graph showing a comparison of energy required for rupture, when an intramedullary rod is used (Example 7) and when an intramedullary rod is not used (Comparative Examples 8, 9).

FIG. 13 is a diagram showing strength test results (a strain-displacement diagram) in a test with an intramedullary rod (Example 7) and a test without an intramedullary rod (Comparative Examples 8, 9), and showing the relationship of movement time of the head and flexural stress values. In FIGS. 13-15, BP denotes Biopex. Because the results of the strength tests in Comparative Examples 8 and 9 were substantially identical, these are shown by a single graph in FIG. 13. As will be clear from FIG. 13, insertion of the intramedullary rod prevented rupture even when subjected to stress for an extended period, demonstrating a clear marked increase in flexural strength.

FIG. 14 shows maximum values of flexural stress in a test with an intramedullary rod (Example 7) and a test without an intramedullary rod (Comparative Examples 8, 9); the maximum values of flexural stress were clearly improved four- to five-fold by inserting the intramedullary rod.

FIG. 15 shows a comparison of energy required for rupture, in a test with an intramedullary rod (Example 7) and a test without an intramedullary rod (Comparative Examples 8, 9). The energy required for rupture was markedly improved by inserting the intramedullary rod.

From the aforedescribed results, it was clear that when the three-dimensional structure produced from a PHA-containing material of the present invention, an intramedullary rod produced from a biodegradable material, and bone cement are employed in combination, strength is markedly improved, as compared with cases in which Biopex, which, while osteoconductive, is susceptible to being broken or bent, is used alone. It is accordingly possible to utilize osteoconductive bone cement even at bone fracture sites that in the past were treated with methyl methacrylate.

INDUSTRIAL APPLICABILITY

Through the use of the three-dimensional structure produced from a PHA-containing material according to the present invention, the bone cement can be prevented from leaking out from the bone during treatment of a bone fracture site. Additionally, due to the heat resistance of the three-dimensional structure produced from a PHA-containing material according to the present invention, bone cements regardless of type, including methyl methacrylate which emits heat during curing, can be prevented from leaking out from the bone, thereby markedly improving the safety of surgery, thus making utilization as a therapeutic material for bone fracture sites possible in medical institutions such as hospitals and urgent care centers, in university medical schools, and such other research institutions or educational institutions.

The invention claimed is:

1. A three-dimensional structure, wherein:
the three-dimensional structure has a pouch form,
the three-dimensional structure is made of non-woven fabric constituted of fibers containing polyhydroxyalkanoate formed by electrospinning,
the fibers have diameters of 5-20 μm,
the fibers constituting the non-woven fabric are not stuck together,
the three-dimensional structure is adapted for preventing leakage of bone cement when the bone cement is injected into a bone fracture site, and
the three-dimensional structure has expandability such that the three-dimensional structure is expanded by 200% or more from an original state when the bone cement is injected at a pressure of 2-4 MPa.

2. The three-dimensional structure according to claim 1, wherein the polyhydroxyalkanoate is a copolymer of at least two monomers selected from 3-hydroxybutyric acid, 3-hydroxyvaleric acid, and 4-hydroxybutyric acid.

3. The three-dimensional structure according to claim 1, wherein the polyhydroxyalkanoate is a copolymer of a monomer of 3-hydroxybutyric acid and a monomer of 3-hydroxyvaleric acid.

4. The three-dimensional structure according to claim 3, wherein a molar ratio of the monomer of 3-hydroxyvaleric acid in the copolymer is 5-50%.

5. The three-dimensional structure according to claim 1, wherein:
the polyhydroxyalkanoate is a copolymer of a monomer of 3-hydroxybutyric acid and a monomer of 4-hydroxybutyric acid, and
a molar ratio of the monomer of 4-hydroxybutyric acid in the copolymer is 5-50%.

6. The three-dimensional structure according to claim 1, wherein the polyhydroxyalkanoate is a copolymer having a molecular weight of 50-3000 kDa.

7. A kit for preparation of a bone filler, including the three-dimensional structure according to claim 1, and a bone cement.

8. The kit for preparation of a bone filler according to claim 7, wherein the bone cement is methyl methacrylate or an osteoconductive material.

9. A kit for preparation of a bone filler, including the three-dimensional structure according to claim 1, an intramedullary rod produced from a biodegradable material, and a bone cement.

10. The kit for preparation of a bone filler according to claim 9, wherein the intramedullary rod is a cylindrically-shaped mesh structure including openings sized to allow bone cement to be exuded.

11. The kit for preparation of a bone filler according to claim 10, wherein the bone cement is methyl methacrylate or an osteoconductive material.

12. The kit for preparation of a bone filler according to claim 9, wherein the bone cement is methyl methacrylate or an osteoconductive material.

13. A method of treating a bone fracture, comprising:
inserting the three-dimensional structure of claim 1 into a hole made in a bone that is to be treated; and
injecting bone cement into the three-dimensional structure inserted into the hole at a pressure of 2-4 MPa so that the three-dimensional structure expands inside the hole and contacts an inner face of the hole and the hole is filled with the bone cement.

14. A method of treating a bone fracture, comprising:
inserting an intramedullary rod into the three-dimensional structure of claim 1;
inserting the three-dimensional structure with the intramedullary rod inserted therein into a hole made in a bone that is to be treated, wherein the intramedullary rod is a cylindrically-shaped mesh structure including openings sized to allow bone cement to be exuded; and
injecting bone cement into the intramedullary rod at a pressure of 2-4 MPa until the three-dimensional structure expands inside the hole and contacts an inner face of the hole and the hole is filled with the bone cement.

* * * * *